United States Patent [19]

Parsons

[11] Patent Number: 4,552,965

[45] Date of Patent: Nov. 12, 1985

[54] 2α, 3β, 4Aβ, 8Aα-DECAHYDRO-3-(4-PHENYL-1-PIPERIDINYL)-2-NAPHTHALENOL

[75] Inventor: Stanley M. Parsons, Santa Barbara, Calif.

[73] Assignee: University of California, Berkeley, Calif.

[21] Appl. No.: 636,183

[22] Filed: Jul. 31, 1984

[51] Int. Cl.$^4$ .......................................... C07D 211/14
[52] U.S. Cl. .................................................. 546/206
[58] Field of Search ........................................ 546/206

[56] References Cited

U.S. PATENT DOCUMENTS 2,352,020  6/1944  Scheving et al. .................. 546/206

OTHER PUBLICATIONS

March, J., *Advanced Organic Chemistry*, McGraw Hill, New York, 1968, p. 334.

Marshall, I. G., *Br. J. Pharmac.*, vol. 38, pp. 503–516 (1970).

*Primary Examiner*—Richard A. Schwartz
*Attorney, Agent, or Firm*—Henderson & Sturm

[57] ABSTRACT

A compound denominated (2α, 3β, 4aβ, 8aα)-decahydro-3-(4-phenyl-1-piperidinyl)-2-naphthalenol(DPPN) having the following chemical structure:

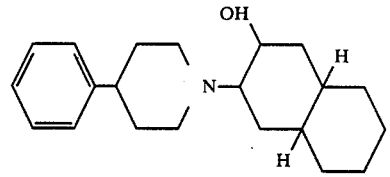

DPPN is more effective than other known compounds in blocking presynaptic release of acetylcholine at cholinergic synapses.

1 Claim, No Drawings

2α, 3β, 4Aβ, 8Aα-DECAHYDRO-3-(4-PHENYL-1-PIPERIDINYL)-2-NAPHTHALENOL

This invention was made with Government support under Grant No. NS-15047 awarded by the Department of Health and Human Services. The Government has certain rights in this invention.

BACKGROUND OF THE INVENTION

1. Field of the Invention

The present invention relates to a new chemical compound for effectively reducing or eliminating the release of acetylcholine (ACh) from the presynaptic nerve terminal of the cholinergic synapse.

Acetylcholine is a neurotransmitter substance, ubiquitous to the animal kingdom, which mediates transmission of electrical impulses from the presynaptic nerve terminal to the postsynaptic target cell whether it be nerve, muscle or organ cell. ACh mediates both inhibitory and excitatory responses depending upon the type of synapse. Synapses are functional junctions between a presynaptic nerve terminal and the postsynaptic membrane of the target cell. Anatomically these cholinergic junctions are comprised of a pre and postsynaptic membrane nexus where said membranes are separated by a microscopic gap or synaptic cleft.

Contained within the presynaptic terminal of the nerve are vesicles which contain ACh. When the presynaptic terminal is depolarized by electrical activity in the presynaptic nerve, such as in a typical monosynpatic excitatory cholinergic synapse, minute quantities of ACh are released from the vesicles to the synaptic cleft. The synaptic vesicles uptake ACh from the nerve cell cytoplasm by active transport across the vesicular membrane in order to replenish the ACh released during repetitive firing of the presynaptic nerve.

The ACh from the synaptic cleft binds to receptors on the postsynaptic membrane which results in an electrical or biochemical response of the target cell, and thus, an effective chemically mediated transmission of the presynaptic electrical impulse is completed to the postsynaptic cell.

The details of the function of acetylcholine and the microanatomy of the synapse has been widely studied. Consequently, many compounds exist for enhancing and inhibiting the effect of ACh by various mechanisms. These mechanisms include both the reduction and the elimination of release of ACh at the presynaptic terminal as well as inhibition of its receptor mediated effect at the postsynaptic membrane. Additionally, the effect of ACh can be enhanced by inhibiting the breakdown of ACh postsynaptically by acetylcholine esterase (AChEase). Those compounds that are effective in blocking acetylcholine esterase effectively block neuroconduction by preventing postsynaptic repolarization. Many common pesticides inhibit the postsynaptic metabolism of acetylcholine by AChEase.

Compounds that affect the action of ACh either presynaptically and postsynaptically also have clinical value as the cholinergic synapse is found in the central nervous system and at the neuromuscular junction of man. Such cholinergic synapses are also partially involved in neural control of the heart and other organs.

2. Prior Art

One such drug for blocking conduction at the neuromuscular junction in mammals is 2-(4-Phenyl-piperidino)-cyclohexanol (AH 5183) which is a tertiary base having the following chemical structure:

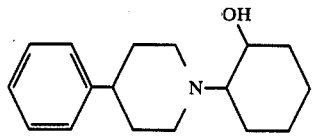

It is believed that AH 5183 inhibits the uptake of newly synthesized ACh into the synaptic vesicles thus producing failure of neurotransmission [see I. G. Marshall, Br. J. Pharmac., Vol. 38, pp. 503–516 (1970)]. While the AH 5183 provides an important research and clinical tool, it is desirable to produce a more effective compound for blocking presynaptic release of acetylcholine. Such a compound would be effective in lower concentrations from those effective for AH 5183.

SUMMARY OF THE INVENTION

The subject matter of the present invention pertains to a newly synthesized compound bearing the chemical formula (2α, 3β, 4aβ, 8aα)-decahydro-3-(4-phenyl-1-piperidinyl)-2-naphthalenol) (DPPN). DPPN has the following chemical structure:

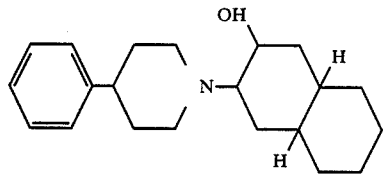

DPPN is approximately four times more effective than AH 5183 in preventing ACh uptake by the vesicles contained within the presynaptic terminal. The present invention also includes the process for synthesizing DPPN.

DETAILED DESCRIPTION

The invention is based upon the synthesis of a new compound, namely DPPN, which utilizes an epoxide precursor, specifically, decahydro-2-naphthalene oxide. The synthesis of this epoxide has been published [see W. J. Johnson, et al., J. Amer. Chem. Soc., Vol. 83, p. 606 (1961); B. Rickborn, et al., J. Org. Chem., Vol. 34, p. 3583 (1969)]. These references and the methods disclosed therein are made part of and incorporated by reference herein.

The best mode of synthesis of DPPN is shown in Example 1 with an alternative mode set forth as Example 2.

EXAMPLE 1

One half gram of 4-phenylpiperidine is dissolved in 2.0 g of decahydro-2-napthalene oxide which is approximately half trans and half cis. This is heated to 90° C. for 18 hours, cooled, and diluted to 20 ml with ethyl ether. A reaction product is precipitated with anhydrous HCl, the precipitate collected by filtration, washed with ethyl ether, and recrystallized twice from ethanol-ethyl ether. Yield is 0.40 g of the hydrochloride with a melting point of 217°–220° C. The structure was confirmed by low resolution electron impact mass spectrometry and by proton magnetic resonance spectrometry. The decalin ring junction sterochemistry was assigned as trans (i.e., 4aβ, 8aα) based on transition state stereochemical considerations. A minor product assumed to be cis decalin (i.e., 4aβ, 8aβ) was not isolated.

EXAMPLE 2

One half gram of 4-phenylpiperidine and 2.0 g of decahydro-2-naphthalene oxide which is approximately half trans and half cis are dissolved in 10 ml of ethanol which is refluxed for 24 hours. After cooling ethanol was removed in vacuo, and the product is chromatographed on silica gel using carbon tetrachloride-chloroform elution. A minor product assumed to be cis decalin (i.e., 4aβ, 8aβ) elutes first followed by the desired product.

Efficacy of DPPN was demonstrated by determining the $IC_{50}$ which is defined as that concentration of an inhibitory drug which reduces an observed physiological phenomenon by 50%. For example, purified *Torpedo californica* electric organ synpatic vesicles uptake ACh in vitro in the presence of ATP. Such vesicles are incubated at room temperature for approximately 30 minutes in isosmotic buffer at neutral PH, the buffer containing approximately 5 mM ATP and 50 μM radioactive ACh, and the radioactivity accumulated by the washed vesicles is then measured by liquid scintillation spectroscopy. By varying the concentration of the compound to be tested to determine its inhibitory effect on ACh uptake, a dose response curve can be deduced including the $IC_{50}$.

In such a Torpedo vesicle preparation, it was shown that AH 5183 had an $IC_{50}$ of 40 μM while DPPN exhibited an $IC_{50}$ of 10 μM. Consequently, AH 5183 would have to be applied in concentrations at least four times greater than DPPN to achieve the comparable physiological affect, namely blockade of vesicular uptake of ACh.

The physiological action of DPPN is believed to be inhibitory at the presnaptic membrane by preventing the release of ACh. The data shows that DPPN provides a more potent alternative to other known ACh presynaptic blockers such as AH 5183. Additionally, DPPN could be utilized as a substitute for those compounds having their inhibitory effect postsynaptically. Therefore, DPPN could also be utilized as an effective pesticide.

I claim:

1. A compound denominated (2α, 3β, 4a β, 8aα)-decahydro-3-(4-phenyl-1-piperidinyl)-2-naphthalenol (DPPN) having the chemical structure:

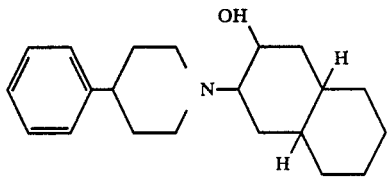

* * * * *